United States Patent [19]

Kavey

[11] Patent Number: 5,502,047
[45] Date of Patent: Mar. 26, 1996

[54] TREATMENT FOR INSOMNIA

[76] Inventor: Neil B. Kavey, 26 W. Orchard Rd., Chappagua, N.Y. 10514

[21] Appl. No.: 34,252

[22] Filed: Mar. 22, 1993

[51] Int. Cl.$^6$ ............... A61K 31/33; A61K 31/335; A61K 31/35

[52] U.S. Cl. ............... 514/183; 514/923; 514/450; 514/453

[58] Field of Search ............... 514/923, 450, 514/453, 183

[56] References Cited

U.S. PATENT DOCUMENTS

| | | | |
|---|---|---|---|
| 3,420,851 | 1/1969 | Bloom et al. | 260/333 |
| 4,110,438 | 8/1978 | Gahwyler | 424/177 |
| 4,434,171 | 2/1984 | Muller | 424/267 |
| 5,030,632 | 7/1991 | Sterling | 514/321 |

OTHER PUBLICATIONS

European Journal of Clinical Pharmacology, vol. 37 pp. 145–150 (1989).
Drugs, vol. 38 (S1) pp. 25–31 (1989).
Journal of Clinical Psychiatry, vol. 51, pp. 298–302 (1990).
Psychopharmacologia vol. 33 pp. 185–202 (1973).
British Journal of Psychiatry vol. 120 pp. 663–672 (1972).
Archives of General Psychiatry vol. 36 pp. 85–90 (1979).
Excerpta Medica International Congress Series vol. 150 pp. 824–826 (1968).
Journal of Clinical Psychiatry vol. 44 (9 Section 2) pp. 25–28 (1983).
Journal of Clinical Pharmacology vol. 9(1) pp. 42–45 (1989).
Physician's Desk Reference pp. 18489–1849 (1990).
Physician's Desk Reference pp. 2434–2435 (1990).
Physician's Desk Reference pp. 1310–1311 (1990).
Sleep Study Abstracts Jan. 1972).
Conn, et al; Pattern of use of Antidepressants in . . . Elderly; Journal of Geriatric Psychology Neurol vol. 5(4), 1992–pp. 228–232.

*Primary Examiner*—T. J. Criares

[57] ABSTRACT

A method for the treatment of chronic insomnia is disclosed which involves the administration of low dosages of a compound selected from the pharmaceutically acceptable forms of doxepin, trimipramine, amitriptyline, trazodone and mixtures hereof.

10 Claims, No Drawings

TREATMENT FOR INSOMNIA

FIELD OF INVENTION

This invention relates to a method for the treatment of individuals suffering from chronic insomnia. In a preferred embodiment, the present invention relates to a method for the treatment of chronic insomnia in individuals other than those suffering from depression.

BACKGROUND OF THE INVENTION

A large percentage of the adult population suffers from insomnia in some form at some time in their lives. This may vary from an occasional episode to chronic conditions and may involve onset and/or maintenance insomnia. Chronic insomnia is typically accepted to involve episodes greater than three (3) weeks in duration. The effects of sleep deprivation resulting from such insomnia are well known and need not be described herein other than to say that they are to be avoided.

Currently, there exist treatments only for acute insomnia. These treatments involve the administration of medication, either of the non-barbiturate or barbiturate type, shortly before bedtime. While both types of sedatives may be used to effectively treat insomnia, neither is without its undesirable side effects. For instance, barbiturate type sedatives, such as secobarbital sodium (sold by Eli Lilly and Company under the tradename of Seconal®) are general depressants. While effective, these medications are well known to lose their effectiveness after a few days. They are further highly addictive and commonly abused. They are therefore no longer widely prescribed.

The group of medications now most commonly used for the treatment of insomnia are the benzodiazepines. There are now 5 such "hypnotics" commonly used. They differ significantly in half lives but are otherwise very similar and equally effective. They have supplanted the barbiturates as the principal treatment for insomnia because they have slightly less addiction potential and are associated with less risk for suicide than the barbiturates unless taken with alcohol. However, this group, too, is know to be effective only for acute or short term insomnia and the medications are not acceptedly used for chronic insomnia. Furthermore, they are also addictive and their wide usage is drawing increasing concern as their potential side effects become more apparent. These include daytime sedation, decreased cognitive abilities such as memory loss and, most recently in the case of Halcion®(triazolam), agitated behavior.

The present invention involves the administration of very small doses of specific known psychotherapeutic agents. These agents include tricyclic compounds and a triazolopyridine derivative which are currently prescribed both for the general treatment of depression and for the treatment of the insomnia component of a depression in individuals suffering from severe depression. These compounds are known to possess a sedative effect in such individuals when administered in moderate to large dosages. However, the use of these compounds at the extremely low dosages claimed herein for the successful treatment of chronic insomnia in otherwise healthy individuals has not been reported and is not obvious in view thereof. For example, the compounds used in the present invention are currently prescribed for a 20–60 year old depressed patient population in dosages varying from about 75 to about 300 milligrams per day of the tricyclic compounds and about 150 to about 600 milligrams per day of the triazolopyridine compound. The entire dosage of such medications are often administered at bedtime. In contrast, the method of the present invention involves the use of a small fraction of such dosage.

OBJECTS OF THE INVENTION

It is an object of the present invention to develop a method for the successful treatment of chronic insomnia.

It is another object of the present invention to develop a method for the successful treatment of insomnia in individuals not suffering from depression.

It is still another object of the present invention to develop a method for the treatment of chronic insomnia using non-addictive medications.

It is a further object of the present invention to develop a method for the treatment of chronic insomnia which does not involve the adverse effects associated with the currently prescribed hypnotics, i.e. residual sedation, lethargy, drowsiness, loss of cognitive ability and/or agitation.

SUMMARY OF THE INVENTION

The present invention is directed to a method for the treatment of a patient suffering from chronic insomnia comprising administering to said patient a compound selected from the group consisting of the pharmaceutically acceptable forms of doxepin, amitriptyline, trimipramine, trazodone and mixtures thereof. The dosage for administration of doxepin, amitriptyline, trazodone, trimipramine and mixtures thereof ranges from about 0.5 to about 20.0 milligrams.

In one preferred embodiment of the present invention, the invention is directed to a method for the treatment of a patient suffering from chronic insomnia comprising administering to said patient doxepin, amitriptyline, trimipramine or mixtures thereof in a dosage of about 10 milligrams or less.

In another preferred embodiment of the present invention, the invention is directed to a method for the treatment of a patient suffering from chronic insomnia comprising administering to said patient trazodone in a dosage of about 15 milligrams or less.

In yet another embodiment, the present invention is directed to a method for the treatment of chronic insomnia in a patient who is not suffering from depression comprising administering to said patient a compound selected from the group consisting of the pharmaceutically acceptable forms of doxepin, amitriptyline, trimipramine, trazodone and mixtures thereof in a dosage ranging from about 0.5 to about 20 milligrams.

DESCRIPTION OF THE INVENTION

The method of the present invention involves the administration of doxepin, amitriptyline, trimipramine, trazodone and mixtures thereof. As noted above, these compounds are well known psychotherapeutic agents which are currently prescribed as antidepressants. Each compound is further readily available commercially. The hydrochloride salt of doxepin is currently marketed by Pfizer Inc. under the tradename Sinequan®. The hydrochloride salt of amitriptyline is currently marketed by Merck & Co., Inc. under the tradename Elavil®. Trimipramine maleate is currently marketed by Wyeth-Ayerst Laboratories under the tradename Surmontil®. The hydrochloride salt of trazodone is currently marketed by Mead Johnson Pharmaceuticals under the tradename Desyrel®.

Of the above compounds which are commercially available as a hydrochloride salt or a maleate in the case of trimipramene, it should be understood that the use of other pharmaceutical salts of such compounds are also within the practice of the present invention. Furthermore, although the above compounds are commercially available in various forms, use of these compounds in other than currently administratable forms (e.g. injectable solutions, capsules, caplets) is also within the scope of the present invention.

As stated above, dosages of doxepin, amitriptyline, trimipramine or mixtures thereof may vary from about 0.5 to about 20.0 milligrams. Preferably dosages of about 10 milligrams or less are utilized. Most preferably, dosages of about 5 milligrams or less are utilized. With respect to trazodone, dosages of about 0.5 to about 20 milligrams are used. Preferably, dosages of about 15 milligrams or less are used. However, as it is recognized that each individual may react differently to a given dose of the medication used herein, the dosages recited herein should be accorded flexibility. Since the point of the present invention is to induce and maintain normal sleep without exposing the patient to residual effect of medication, the lowest effective dosage of the compounds are to be utilized whenever possible.

Administration of the compounds should take place within about one hour before bedtime. Again, the onset of the sedative effect will vary with the individual and the dosage prescribed.

"Depression" as used herein refers to a psychiatric diagnosis of depression and includes those disorders categorized under depression in the Psychiatric Diagnostic and Statistical Manual 3, American Psychiatric Association Press.

The following Examples are offered to illustrate the claimed method and its practice. They should not however be construed in any way as a limitation to the scope of the present invention.

EXAMPLE 1

The patient was a thirty-eight year old female who suffered from maintenance insomnia for one year. She had been treated previously with "hypnotics" and, at the time of presentation, was using diphenhydramine 50–100 mg hs without success. Psychotherapy had also failed to relieve the insomnia. At the time of consultation, she had normal affect with no depression, anxiety or substance overuse. She was started on doxepin 10 mg hs. Follow up at 30 days revealed her to be sleeping well. An attempt to decrease the dosage produced a return of the insomnia. She is currently maintained on 10 mg of doxepin and is doing well.

EXAMPLE 2

The patient was a fifty-two year old female with a maintenance insomnia of three years' duration. She had tried several therapeutic modalities including dalmane 15 mg hs, hypnosis, and a behavioral program all without improvement. At the time of presentation, affect was normal and there was no depression or anxiety. Alcohol use was not a factor. She was prescribed doxepin 5 mg hs which produced an immediate resolution of the disturbed sleep. The doxepin was subsequently discontinued and the insomnia returned. She was restarted on doxepin at 5 mg hs and the insomnia again was relieved. Maintenance is ongoing at this dosage.

EXAMPLE 3

The patient was a fifty-two year old male with a longstanding maintenance insomnia. He had been treated with temazepam 15 mg hs for many years but was suffering memory loss and had a fear of addiction. Clinical evaluation revealed normal affect without depression, anxiety, or substance use. He was started on doxepin 10 mg hs which rapidly restored sound, uninterrupted sleep. An attempt to lower the dosage ended with a return of the insomnia. The dosage level was increased back to 10 mg with resolution of the sleep disturbance. He is currently maintained at that dosage and is doing well.

EXAMPLE 4

The patient was a forty-nine year old female with a maintenance insomnia of two years' duration. She had previously been treated with diazepam for anxiety and the insomnia with no effect on the latter. She had a past history of depression but had normal affect and no depression at her initial consultation or during her treatment. Alcohol use was not significant. She was started on doxepin 12.5 mg hs upon which the insomnia was resolved. At long term follow up there was no sleep complaint at this dosage.

EXAMPLE 5

The patient was a sixty-five year old male retiree with an onset and maintenance insomnia of thirty years' duration. He had attempted self-treatment unsuccessfully with several over-the-counter preparations. Prescription "sleeping pills" has been similarly ineffective. At the time of presentation, the patient had a normal affect with no anxiety, depression, or substance abuse. Therapy was initiated with doxepin 10 mg hs which effected undisturbed and restful sleep. He is now maintained on doxepin 8 mg hs and is doing well.

EXAMPLE 6

The patient was a fifty-four year old male who had developed a maintenance insomnia. He had been previously treated with alprazolam 0,125 mg hs without improvement. A behavioral program combined with attempted withdrawal from the alprazolam was ineffective. Clinical evaluation revealed a normal affect and mental status, and an absence of depression, anxiety and substance abuse. He was started on doxepin 5 mg hs which produced a clinical cure. After two years at this dosage, he continues to sleep well and has experienced no adverse effects from the medication.

I claim:

1. A method for the treatment of a patient suffering from chronic insomnia comprising administering to said patient a compound selected from the group consisting of doxepin and pharmaceutically acceptable salts thereof in a daily dosage ranging from about 0.5 to about 20 milligrams.

2. The method of claim 1 wherein the pharmaceutically acceptable salt of doxepin is the hydrochloride salt thereof.

3. The method of claim 1 where the daily dosage is about 0.5 to about 10 milligrams.

4. The method of claim 1 where the daily dosage is about 0.5 to about 5 milligrams.

5. The method of claim 2 where the daily dosage is about 0.5 to about 10 milligrams.

6. The method of claim 2 where the daily dosage is about 0.5 to about 5 milligrams.

7. The method of claim 1 wherein the patient is suffering from depression.

8. The method of claim 1 wherein the patient is suffering from depression.

9. The method of claim 4 wherein the patient is not suffering from depression.

10. The method of claim 5 wherein the patient is not suffering from depsression.

* * * * *

(12) EX PARTE REEXAMINATION CERTIFICATE (5318th)
United States Patent
Kavey

(10) Number: US 5,502,047 C1
(45) Certificate Issued: Apr. 4, 2006

(54) TREATMENT FOR INSOMNIA

(75) Inventor: Neil B. Kavey, Chappagua, NY (US)

(73) Assignee: Procom One, Inc., Steamboat Springs, CO (US)

Reexamination Request:
No. 90/006,950, Feb. 25, 2004

Reexamination Certificate for:
Patent No.: 5,502,047
Issued: Mar. 26, 1996
Appl. No.: 08/034,252
Filed: Mar. 22, 1993

(51) Int. Cl.
*A61K 31/33* (2006.01)
*A61K 31/335* (2006.01)
*A61K 31/35* (2006.01)

(52) U.S. Cl. .................. 514/183; 514/450; 514/453; 514/923

(58) Field of Classification Search .............. 514/183, 514/450, 453, 923
See application file for complete search history.

(56) References Cited

PUBLICATIONS

Roth, Thomas, et al., "Psychopharmacology: The Effects of Doxepin HCl on Sleep and Depression," *J. Clin. Psychiatry* 43:9, pp. 366–368, Sep. 1982.
Charles Lapp, "Chronic Fatigue Syndrome is a Real Disease", North Carolina Family Physician, Winter 1992, vol. 43, No. 1.

*Primary Examiner*—Shengjun Wang

(57) ABSTRACT

A method for the treatment of chronic insomnia is disclosed which involves the administration of low dosages of a compound selected from the pharmaceutically acceptable forms of doxepin, trimipramine, amitriptyline, trazodone and mixtures hereof.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–7, 9 and 10 are cancelled.

Claim 8 is determined to be patentable as amended.

New claims 11–25 are added and determined to be patentable.

8. [The method of claim 1] *A method for the treatment of a patient suffering from chronic insomnia comprising administering to said patient a compound selected from the group consisting of doxepin and pharmaceutically acceptable salts thereof in a daily dosage ranging from about 0.5 to about 20 milligrams* wherein the patient is suffering from depression *and the insomnia is a component of the depression*.

*11. The method of claim 8 wherein the daily dosage is about 0.5 to about 9 milligrams.*

*12. The method of claim 8 wherein the daily dosage is about 0.5 to about 4 milligrams.*

*13. A method for the treatment of a patient suffering from chronic insomnia comprising administering to said patient a compound selected from the group consisting of doxepin and pharmaceutically acceptable salts thereof in a daily dosage ranging from about 0.5 to about 20 milligrams wherein the patient is otherwise healthy.*

*14. The method of claim 13 wherein the daily dosage is about 0.5 to about 10 milligrams.*

*15. The method of claim 13 wherein the daily dosage is about 0.5 to about 5 milligrams.*

*16. The method of claim 13 wherein the daily dosage is about 0.5 to about 9 milligrams.*

*17. The method of claim 13 wherein the daily dosage is about 0.5 to about 4 milligrams.*

*18. The method of claim 13 wherein the daily dosage is about 3 milligrams.*

*19. A method for the treatment of a patient suffering from chronic insomnia comprising administering to said patient a compound selected from the group consisting of doxepin and pharmaceutically acceptable salts thereof in a daily dosage ranging from about 0.5 to about 4 milligrams.*

*20. The method of claim 19 wherein the daily dosage is about 0.5 to about 3 milligrams.*

*21. The method of claim 19 wherein the daily dosage is about 0.5 to about 2.5 milligrams.*

*22. The method of claim 19 wherein the daily dosage is about 0.5 to about 2 milligrams.*

*23. The method of claim 19 wherein the pharmaceutically acceptable salt of doxepin is the hydrochloride salt thereof.*

*24. The method of claim 19 wherein the patient is not suffering from depression.*

*25. The method of claim 19 wherein the patient is suffering from depression.*

* * * * *